United States Patent
Rouns et al.

(10) Patent No.: US 6,588,425 B2
(45) Date of Patent: Jul. 8, 2003

(54) RESPIRATORY SUCTION CATHETER APPARATUS WITH ANTIMICROBIAL CHAMBER

(75) Inventors: Cameron G. Rouns, South Jordan, UT (US); Tim J. Way, Bothell, WA (US); L. John Teuscher, Springville, UT (US); Edward B. Madsen, Riverton, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 143 days.

(21) Appl. No.: 09/745,287

(22) Filed: Dec. 21, 2000

(65) Prior Publication Data

US 2002/0078963 A1 Jun. 27, 2002

(51) Int. Cl.[7] ............................................. A61M 16/00
(52) U.S. Cl. ............................ 128/207.14; 128/200.26; 128/207.16; 604/35
(58) Field of Search ....................... 128/207.16, 205.24, 128/207.14, 205.19, 912, 200.26, 201.13, 205.12, 205.27, 202.27; 604/190, 251, 252, 264, 268, 523, 533, 534, 535, 537, 35, 19

(56) References Cited

U.S. PATENT DOCUMENTS

| | | |
|---|---|---|
| 3,606,889 A | 9/1971 | Arblaster |
| 4,507,118 A | 3/1985 | Dent |
| 4,592,920 A | 6/1986 | Murtfeldt |
| 4,623,329 A | 11/1986 | Drobish et al. |
| 4,677,143 A | 6/1987 | Laurin et al. |
| 4,834,711 A | 5/1989 | Greenfield et al. |
| 5,140,983 A | 8/1992 | Jinotti |
| 5,213,096 A * | 5/1993 | Kihlberg et al. ........ 128/205.12 |
| 5,354,267 A * | 10/1994 | Niermann et al. ...... 128/207.14 |
| 5,460,172 A * | 10/1995 | Eckerbom et al. ...... 128/201.13 |
| 5,624,704 A | 4/1997 | Darouiche et al. |
| 5,638,812 A | 6/1997 | Turner |
| 5,681,575 A | 10/1997 | Burrell et al. |
| 5,715,815 A * | 2/1998 | Lorenzen et al. ...... 128/207.14 |
| 5,730,123 A * | 3/1998 | Lorenzen et al. ...... 128/200.26 |
| 5,735,271 A * | 4/1998 | Lorenzen et al. ...... 128/200.26 |
| 5,779,687 A * | 7/1998 | Bell et al. .............. 128/207.16 |
| 5,820,607 A | 10/1998 | Tcholakian et al. |
| 5,901,705 A * | 5/1999 | Leagre ................... 128/207.14 |
| 6,039,940 A * | 3/2000 | Perrault et al. ............. 424/443 |
| 6,105,576 A * | 8/2000 | Clawson et al. ........ 128/201.13 |
| 6,117,285 A | 9/2000 | Welch et al. |
| 6,415,788 B1 * | 7/2002 | Clawson et al. ........ 128/201.13 |

OTHER PUBLICATIONS

U. S. patent application No. 09/716,486, Filed Nov. 20, 2000.

U. S. patent application No. 09/741,769, Filed Dec. 19, 2000.

* cited by examiner

Primary Examiner—Weilun Lo
Assistant Examiner—Mital Patel
(74) Attorney, Agent, or Firm—Dority & Manning, P.A.

(57) ABSTRACT

A cartridge for use on a medical apparatus is provided and includes a body having a proximal chamber and a distal chamber. An antimicrobial agent is disposed in one of the distal or proximal chambers. A port is located on the body and communicates with the chamber in which the antimicrobial agent is disposed. In another embodiment, another port is located in the other chamber. Also, a respiratory suction apparatus is provided that is fitted with a cartridge mentioned above.

38 Claims, 9 Drawing Sheets

RESPIRATORY SUCTION CATHETER APPARATUS WITH ANTIMICROBIAL CHAMBER

TECHNICAL FIELD

The present invention relates to suction catheters, and more particularly to a suction catheter having an antimicrobial chamber.

BACKGROUND

A variety of different circumstances exist in which a person may be required to have a catheter inserted into their body for a medical procedure. One such use for a catheter exists when a person needs to have an artificial airway, such as an endotracheal tube, placed in his or her respiratory system. During surgery, for instance, the artificial airway's primary function is to keep the patient's airway open so that adequate lung ventilation can be maintained during the surgical procedure. Alternatively, with many patients, the endotracheal tube will remain in place to sustain mechanical ventilation for a prolonged period.

If an endotracheal tube is to be left in place for any substantial amount of time, it is critical that respiratory secretions be periodically removed. This is usually accomplished with the use of a respiratory suction catheter. As the suction catheter is withdrawn, a negative pressure is applied to the interior of the catheter to draw mucus and other secretions from the respiratory system.

While a substantial amount of mucus will be withdrawn through the catheter lumen, a portion of the mucus will remain on the outside of the catheter for a variety of reasons, it is important that any mucus and secretions be cleaned off the catheter tube, for example to prevent contamination from infectious agents that may be present in the respiratory secretions.

Several mechanisms exist by which a catheter may be cleaned. For example, a lavage port may be included which enables the clinician to inject liquid into the area surrounding the tip of the catheter after it has been withdrawn from the patient. When liquid is injected into a closed suction catheter apparatus and suction is applied, the liquid helps to loosen and remove the secretions from the exterior of the catheter.

One significant problem with simply injecting liquid and applying suction to remove it, is that the suction also causes a volume of respiratory air to be removed through the catheter. In a "closed system", the air that is evacuated potentially disrupts the carefully controlled ventilatory cycle. Therefore, the amount of respiratory air available to the patient is decreased as a result of catheter cleaning.

One way to control potential contamination from respiratory secretions is to introduce antimicrobial agents to inhibit the proliferation of bacteria in the respiratory apparatus, and especially on the catheter itself. The problem with surface bonding of the agent onto the catheter is that it is limited to short term delivery of the pharmacologically active ingredient.

Therefore, there is a need in the art for a closed suction respiratory system that is capable of effectively cleaning the tip of a suction catheter without a resultant drop in ventilation air to the patient. Additionally, a need in the art exists in applying an antimicrobial compound into the closed suction respiratory system quickly, effectively, and for a sustained amount of time.

SUMMARY

Objects and advantages of the invention will be set forth in part in the following description, or may be obvious from the description, or may be learned from practice of the invention.

The present invention provides for a cartridge that can be used with not only a respiratory system, but with other medical apparatuses. Examples of such would include lavage systems and instrumentation to monitor and view the respiratory or digestive tract.

As used herein, the term "proximal" refers to a direction toward the clinician, and the term "distal" refers to a direction towards the patient.

According to the invention, the cartridge for use on a medical apparatus includes a body which has a proximal end and a distal end. The body also has a passageway that leads from the proximal to the distal end. This passageway accommodates the insertion and retraction of a surgical instrument through the cartridge. The passageway and the proximal end define a proximal chamber, while the passageway and the distal end define a distal chamber. A proximal port is located on the body which communicates with the proximal chamber. A distal port is located on the body which communicates with the distal chamber. An antimicrobial agent is disposed in either the proximal or the distal chambers.

In an alternate embodiment, only one port is provided which communicates with the chamber in which the antimicrobial agent is disposed.

Also according to the invention, a respiratory suction apparatus is provided. The apparatus consists of a suction catheter for removing fluids from a respiratory tract of a patient by insertion of a distal end of the suction catheter into the respiratory tract. Fluids are removed by withdrawing the distal end of the suction catheter through a portion of the tract while applying negative pressure to a lumen of the suction catheter. A cartridge as discussed previously is incorporated in-line in the apparatus so that the catheter passes through the cartridge. For example, the cartridge may be connected to a manifold located distally of the cartridge. The manifold is configured for communication with a artificial airway fitting structure attached to a patient.

In an alternative embodiment of the invention, a single flap valve is located distally of the cartridge. The flap valve substantially isolates the suction catheter from the manifold upon withdrawing the distal portion of the suction catheter from the manifold and past the flap valve.

BRIEF DESCRIPTION OF THE DRAWINGS

Embodiments of the present invention are described by way of example with reference to the accompanying drawings in which.

DETAILED DESCRIPTION

Reference will now be made in detail to embodiments of the invention, one or more examples of which are illustrated in the drawings. Each example is provided by way of explanation of the invention, and is not meant as a limitation of the invention. For example, features illustrated or described as part of one embodiment can be used with another embodiment to yield still a third embodiment. It is intended that the present invention include such modifications and variations.

The present invention provides a device to quickly and effectively apply an antimicrobial agent into a closed suction respiratory system. Further, the invention also solves the need of applying such an application of antimicrobial agent to a closed suction respiratory system while at the same time providing for a way to clean the tip of a suction catheter without a resultant drop in ventilation air to the patient.

A cartridge is provided that houses an antimicrobial hydrogel that acts as an antimicrobial wipe when a surgical instrument is extended or retracted through the cartridge. Although capable of being used on various types of medical instrumentation, the cartridge will be described as being incorporated into a suction catheter respiratory system for sake of explaining the invention through one embodiment thereof. It is to be understood that the option exists to use the cartridge for various types of catheters and other surgical instrumentation.

Figure 1:
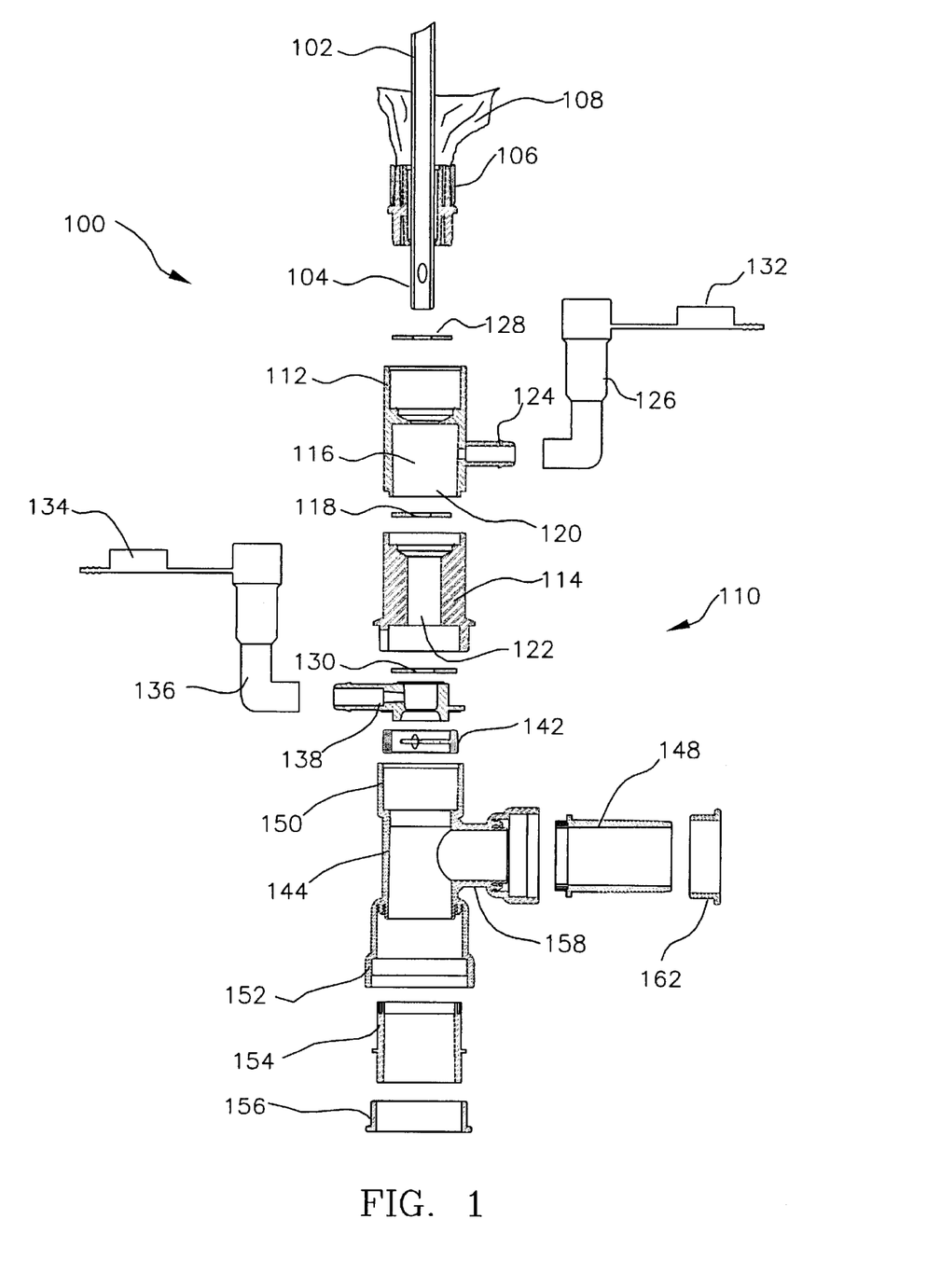
FIG. 1 is an exploded cross-section view of a respiratory suction apparatus of the present invention. The drawing shows a suction catheter with a cartridge being attached to a flapper valve and a T-shaped manifold.

Referring now to the drawings, FIG. 1 shows an exploded view of a cartridge 110 incorporated into a respiratory suction apparatus indicated generally at 100. The respiratory suction apparatus 100 consists of a suction catheter 102 that is inserted through the respiratory suction apparatus 100 and into the respiratory tract of a patient. The suction catheter 102 is typically used to remove mucus and other secretions from the respiratory tract of a ventilated patient. The suction catheter 102 has a distal end 104. A protective sleeve 108 is provided to contain and isolate contaminants and mucus that accumulate on the suction catheter as it is withdrawn from the respiratory tract. The protective sleeve 108 is provided with a sealing connection 106 that attaches the protective sleeve 108 portion of the respiratory suction apparatus 100 to the cartridge 110.

The cartridge 110 is shown with a body portion that includes a proximal end 112 and a distal end 114. A passageway 116 is formed through the body of the cartridge 110. The passageway 116 allows for the insertion and retraction of the suction catheter 102 through the cartridge 110. The body of the cartridge 110 and the passageway 116 may be cylindrical in shape.

The cartridge 110 is also provided with a middle seal 118 that separates the proximal end 112 from the distal end 114. A proximal seal 128 and distal seal 130 are provided on the proximal end 112 and distal end 114, respectively, of the cartridge 110.

The middle seal 118, the passageway 116, and the proximal end 112 define a proximal chamber 120 in the body. The middle seal 118, the passageway 116, and the distal end 114 define a distal chamber 122 in the body. Although not shown in FIG. 1, an antimicrobial agent is disposed in the proximal chamber 120. A port 124 is located on the body in communication with the proximal chamber 120. A housing member 126 may be connected to the port 124 and provided with a cap 132 to close the housing member 126 when saline is not applied to the respiratory suction apparatus 100 through the port 124.

The distal end 114 of the body of the carriage 110 connects to a valve retainer 138. Valve retainer 138 has the distal seal 130 at one end, and a flapper valve 142 at the other end. The flapper valve 142 is discussed in greater detail in co-pending and commonly owned U.S. application Ser. No. 09/716,486, entitled "Respiratory Suction Catheter Apparatus with Improved Valve and Collar". This application is incorporated herein in its entirety for all purposes.

The valve retainer 138 is provided with a port that attaches to an irrigation housing 136. A distal port housing member 136 is provided with a cap 134 used to close the housing 136 when the respiratory suction apparatus 100 is not being cleaned.

A T-shaped manifold is indicated at 144. The manifold 144 has a port 150 located on one end that interacts with the valve retainer 138 and houses the flapper valve 142. At the other end of the manifold 144, a port 152 to the respiratory tract is present. A swivel insert 154 interacts with port 152. A lock ring 156 is provided to encase swivel insert 154. This arrangement allows for the respiratory suction apparatus 100 to be rotated about an artificial airway connection to the respiratory tract without undo strain or discomfort to the patient.

On the side of the T-shaped manifold 144, a ventilation port 158 is provided. A swivel insert 148 interacts with the port 158. A lock ring 162 locks the swivel insert 148 onto the port 158.

Figure 2:
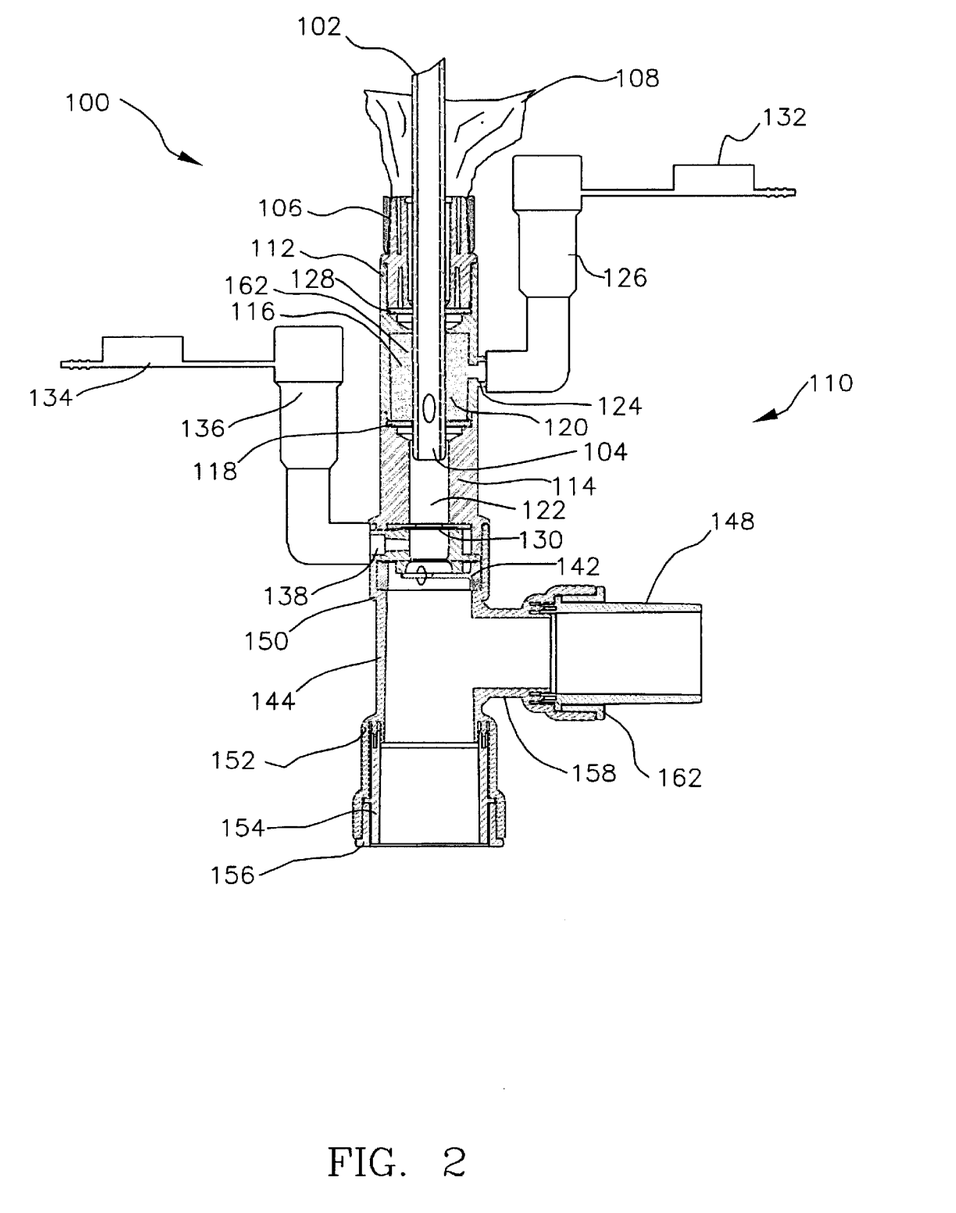
FIG. 2 is a cross-section view of the respiratory suction apparatus of FIG. 1 in an assembled state.

FIG. 2 shows an assembled view of the respiratory suction apparatus 100 of FIG. 1. The elements, numbers, and connections are the same as in FIG. 1. However, FIG. 2 also shows the antimicrobial agent 162 disposed within proximal chamber 120.

Figure 3:
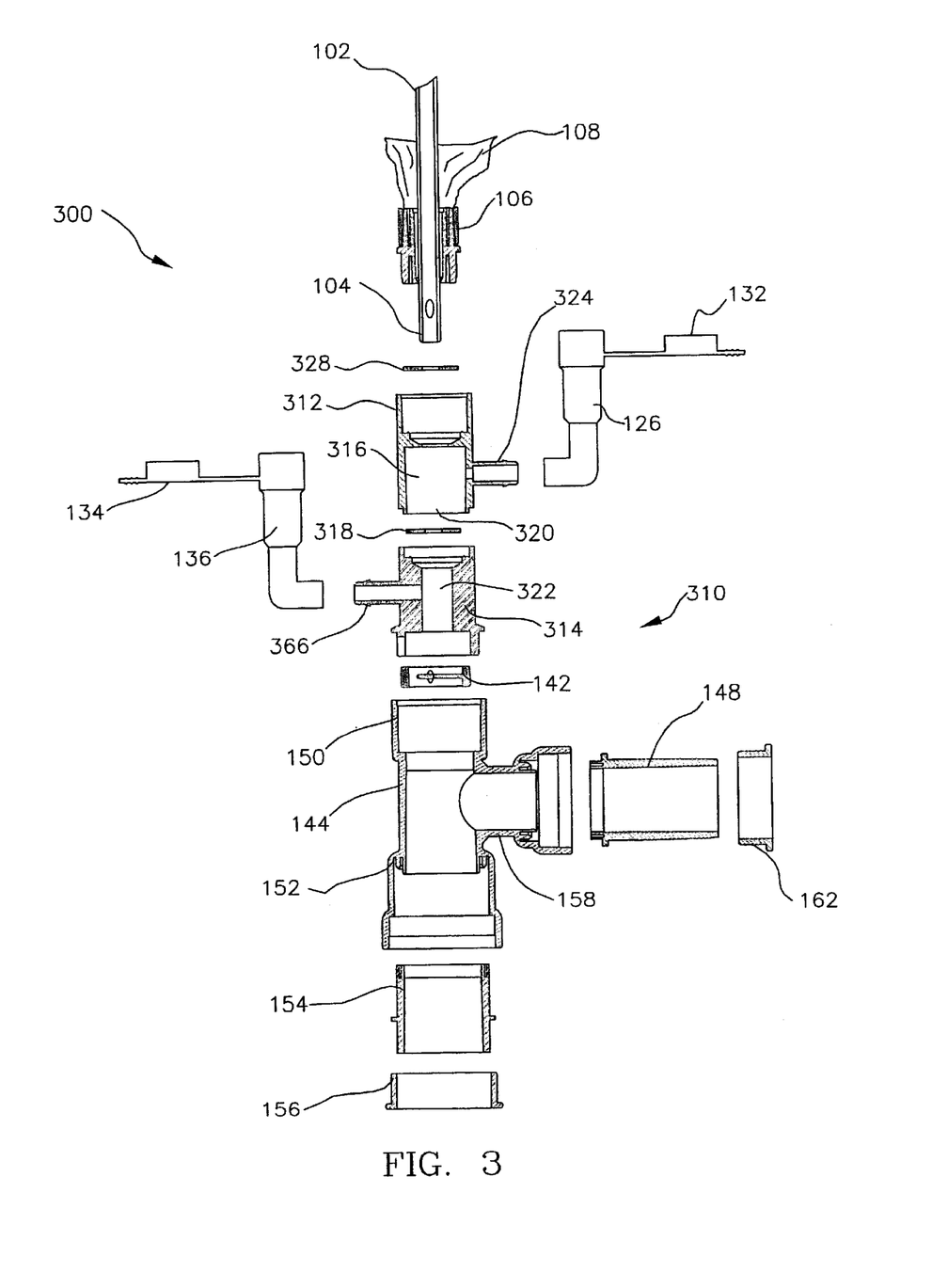
FIG. 3 is an exploded cross-section view of an alternate embodiment of a respiratory suction apparatus of the present invention. The drawing shows a suction catheter with a cartridge being attached to a flapper valve and a T-shaped manifold.

FIG. 3 shows an alternate embodiment of a respiratory suction apparatus 300 of the present invention. The suction catheter 102, manifold 144, and flapper valve 142 are the same as discussed above. A cartridge is indicated generally at 310. The cartridge 310 consists of a body that has a proximal end 312 and a distal end 314. A passageway 316 leads through the body. The passageway 316 allows for the suction catheter 102 to be inserted through and retracted from the cartridge 310. A proximal seal 328 is located at the proximal end 312 of the body. A distal seal 318 is located distally from the proximal seal 328. The distal seal 318 is also located inside the body of the cartridge 310.

The body of the cartridge 310, the proximal seal 328 and the distal seal 318 define a proximal chamber 320. The body of the cartridge 310, the distal seal 318 and the distal end 314 of the body define a distal chamber 322. A proximal port 324 is located on the body that communicates with the proximal chamber 320. A housing 126 is attached to the proximal port 324. A cap 132 is attached to the housing 126 and is in the closed position when the respiratory suction apparatus 300 is not being used.

A distal port 366 is located on the body of the cartridge 310. The distal port 366 is in communication with the distal chamber 322. A housing 136 is connected to distal port 366. A cap 134 is attached to the housing 136 and is in the closed position when the respiratory suction apparatus 300 is not being used.

Figure 4:
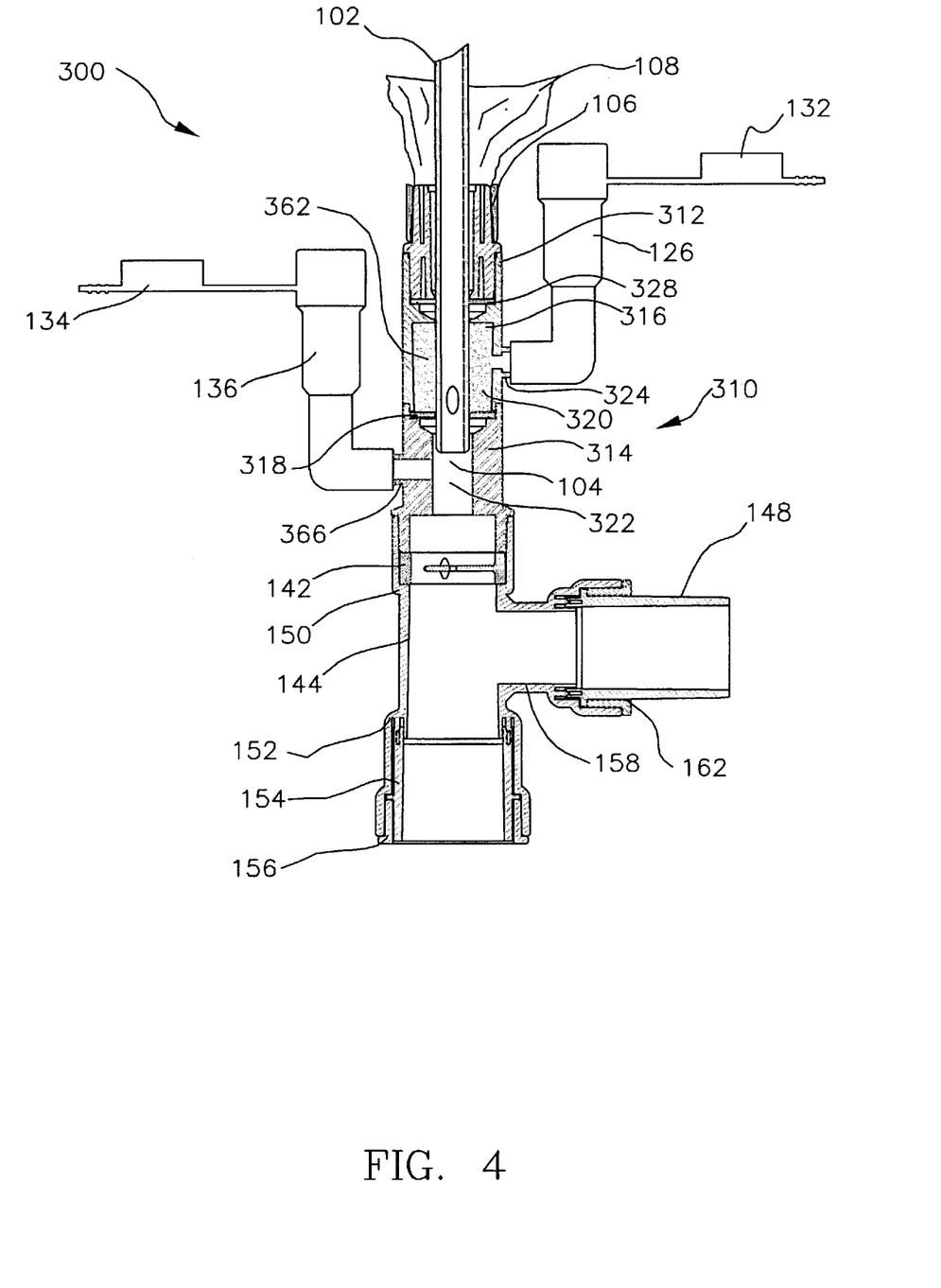
FIG. 4 is a cross-section view of the respiratory suction apparatus of FIG. 3 in an assembled state.
Figure 5A:
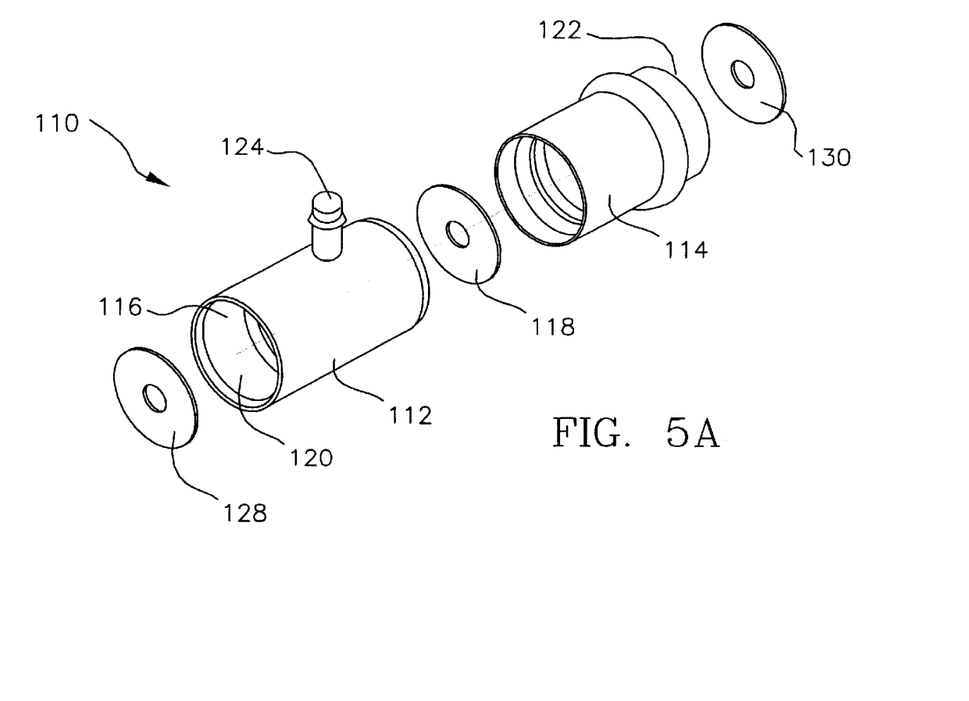
FIGS. 5A and 5B show an exploded perspective view and an assembled cross-section view, respectively, of the cartridge of FIG. 1.
Figure 5B:
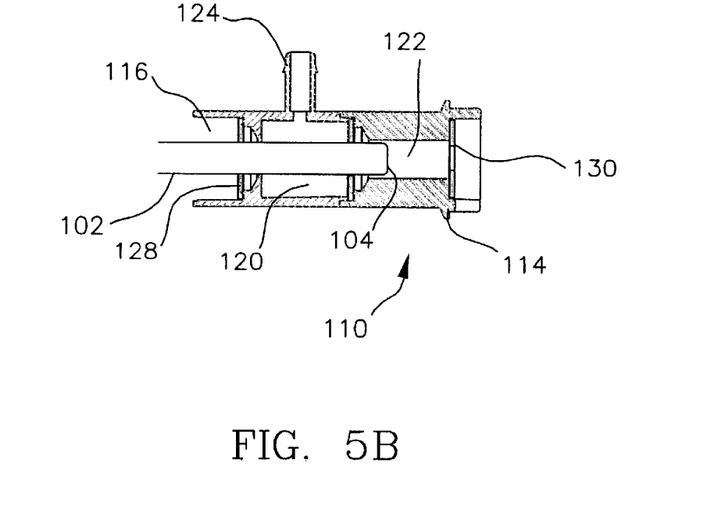

FIG. 4 shows an assembled view of the respiratory suction apparatus 300 of FIG. 3. The only additional element shown in FIG. 4 is the antimicrobial agent 362 shown disposed within the proximal chamber 320.

The antimicrobial agent of the present invention can be a hydrogel. This hydrogel can be applied in layers to the body in the proximal chamber 360. Further, the antimicrobial agent 362 can be a quaternary amine hydrogel that incorporates antimicrobial properties. Here the quaternary amine hydrogel is cured by a redox method on the interior of the body of the cartridge 310. Alternatively, the quaternary amine hydrogel can be cured by an ultraviolet catalyst method on the body of the cartridge 310. Alternatively, other methods known in the art may be used to dispose the hydrogel inside the body.

In the embodiment of FIG. 4, the antimicrobial agent 362 is disposed in the proximal chamber 320. Saline or sterile water is introduced into the proximal chamber 320 through the proximal port 324 and housing 126. The saline is used to hydrate the antimicrobial agent 362. Hydration of the hydrogel causes it to swell inside of the proximal chamber 320 such that passage of the suction catheter 102 through the proximal chamber 320 with the antimicrobial agent 362 causes a wiping process to occur that reduces the occurrence of microbial colonization on the suction catheter 102. This wiping process reduces the chances of patient and clinician infection from the patient's respiratory fluids.

The proximal seal 328 acts as a barrier to isolate the proximal chamber 320 and the antimicrobial agent 362 from the protective sleeve 108 and the connection from the protective sleeve to the cartridge 106. The distal seal 318 is used to isolate the antimicrobial agent 362 from the distal chamber 322. Further, the distal seal 318 acts as a wiping seal to remove secretions from the suction catheter 102 as it is withdrawn distally from the artificial airway. The distal seal 318 also helps to define a cleaning chamber that is further defined by the flapper valve 142 and the distal chamber 322.

The distal end 104 of the suction catheter is placed against the flapper valve 142. The cleaning process is described in detail in commonly owned U.S. patent application Ser. No. 09/741,769, entitled "Turbulent Air Cleaning Method and Apparatus for Catheter Assembiies". This application is incorporated by reference herein for all purposes. A cleaning solution is introduced to the distal port housing 136 and passed through the distal port 366 into the distal chamber 322. Introduction of a cleaning solution and application of suction to the suction catheter 102 creates a cleaning procedure to clean the distal end of the catheter 104.

Figure 8:
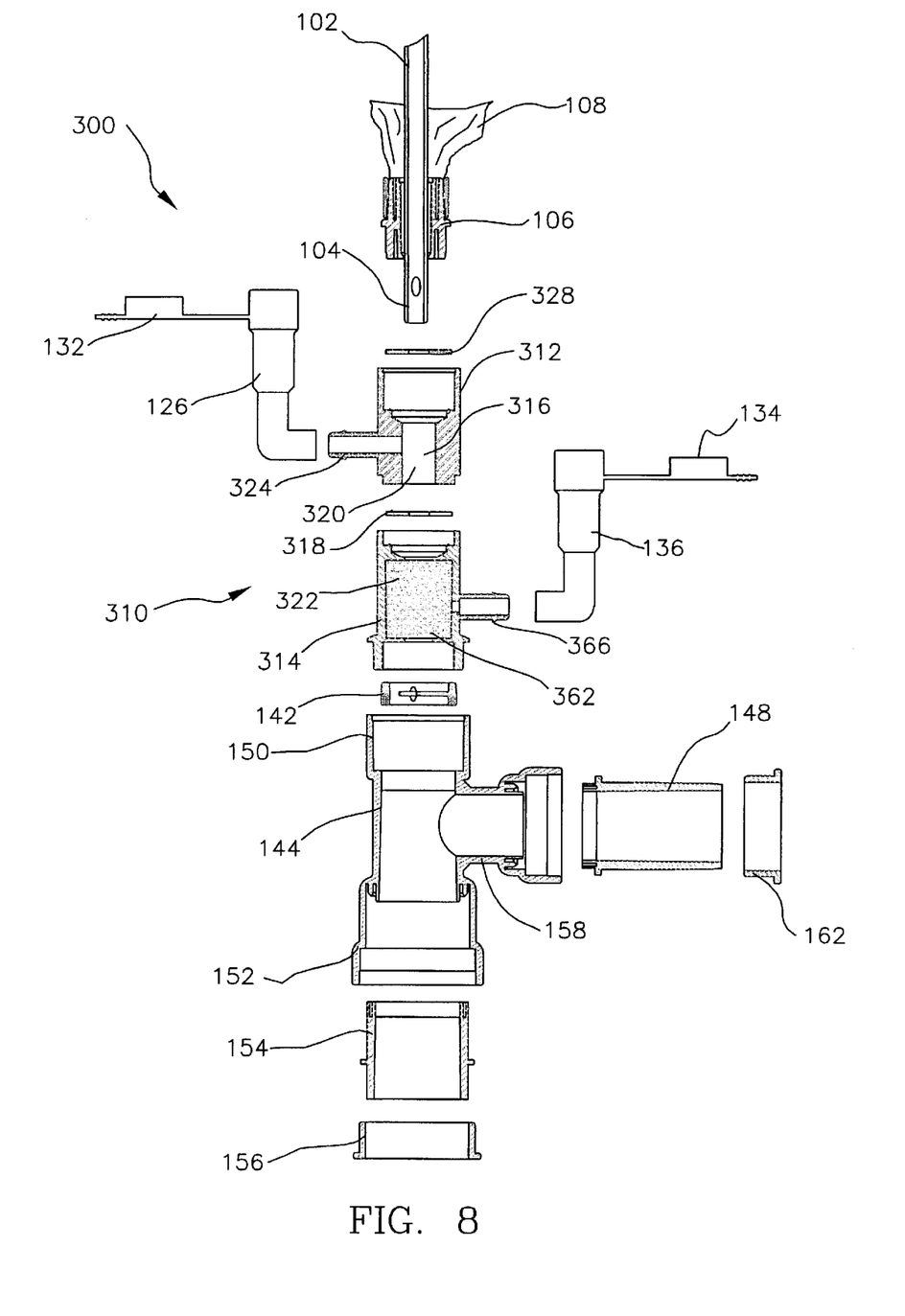
FIG. 8 is an exploded cross-sectional view of an alternate embodiment of a respiratory suction apparatus of the present invention. The drawing shows the antimicrobial agent disposed in a chamber distal to the chamber in which it is disposed in FIG. 3.

It is also to be understood that the present invention defines a cartridge 310 that has the antimicrobial agent 362 disposed in the distal chamber 322 as opposed to the proximal chamber 320. Such an arrangement is shown in FIG. 8. In this embodiment, the suction catheter 102 can be cleaned in the proximal chamber 320 of the cartridge 310.

The suction catheter 102 can be wiped with the antimicrobial agent 362 as it is passed through the distal chamber 322.

It should be understood that the proximal chamber 320 and the proximal end of the body 312 are configured differently between FIG. 3 and FIG. 8 due to the fact that one houses the antimicrobial agent 362 and the other acts as a cleaning chamber. The same holds true for the distal chamber 322 and the distal end of the body 314 between the embodiments shown in FIGS. 3 and 8.

Referring to the embodiments shown in FIGS. 1 and 2, as the catheter 102 is withdrawn through the distal chamber 122, the middle seal 118 wipes secretions and mucus from the suction catheter 102. These secretions are contained in the distal chamber 122, and can be removed by either suction through the suction catheter 102 or by lavage introduced through the irrigation housing 136. As discussed with the previous embodiment, the present invention also includes an embodiment (FIG. 8) in which the antimicrobial agent 362 is disposed in the distal chamber 322 of the cartridge 310 as opposed to the proximal chamber 320. In such an embodiment, a wiping process occurs on the suction catheter 102 as it passes through the distal chamber 322. Hydrate will be applied through distal port housing 136 to hydrate the antimicrobial agent 362. The suction catheter 102 can be cleaned in the proximal chamber 320.

The cartridge of the present invention can be applied to not only respiratory suction catheter apparatuses, but to other medical systems and used with other medical instruments. Such a cartridge 110 is shown in FIGS. 5A, 5B, 7A, and 7B. Although a suction catheter 102 is shown inserted into the cartridge 110, it is to be understood that other medical instruments may be cleaned with the cartridge of the present invention.

Figure 6:
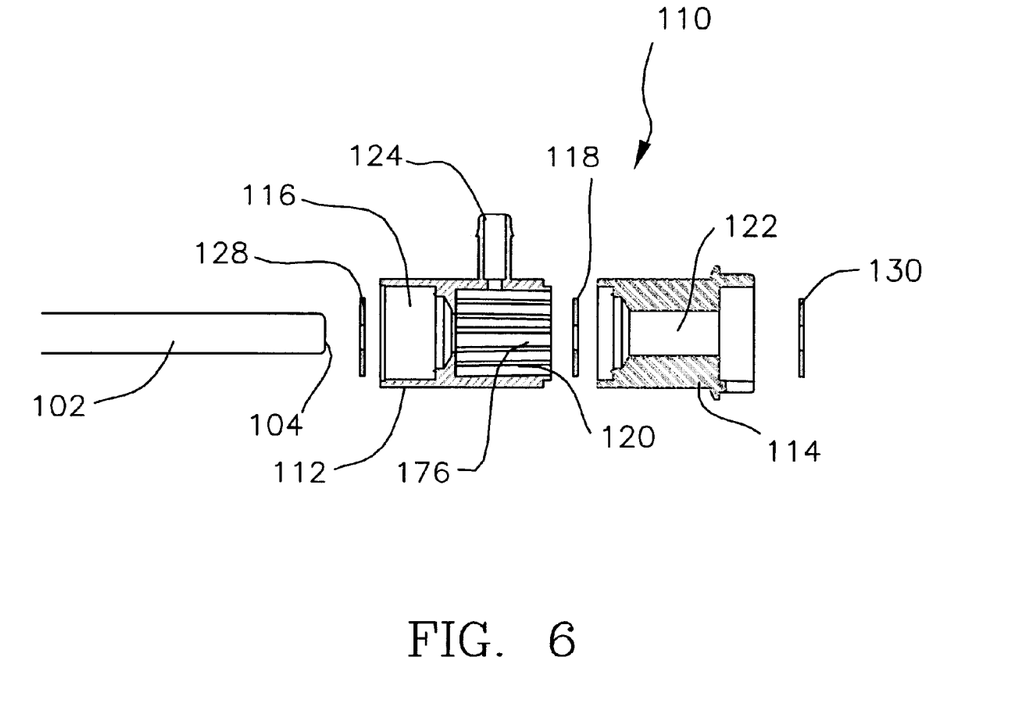
FIG. 6 shows an exploded cross-section view of the cartridge of FIG. 5 having a recess feature.
Figure 7A:
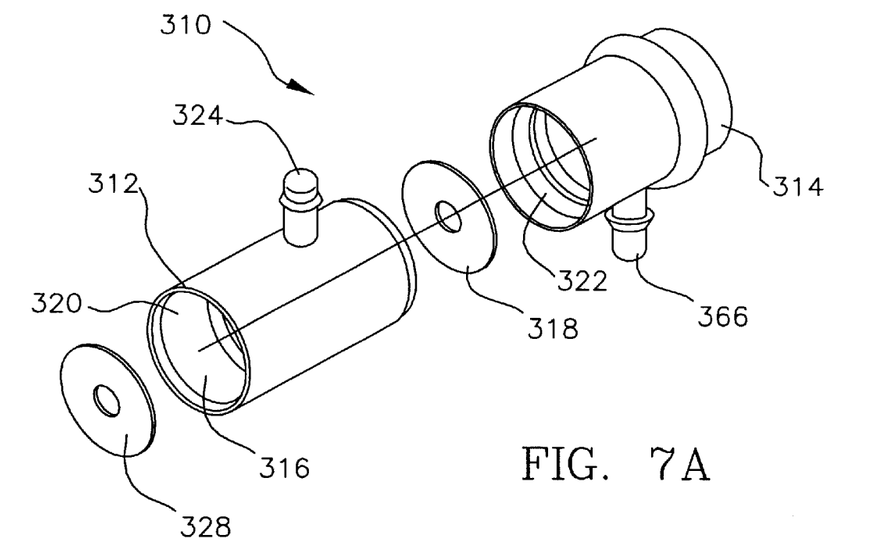
FIGS. 7A and 7B show an exploded perspective view and an assembled cross-section view, respectively, of the cartridge of FIG. 3.
Figure 7B:
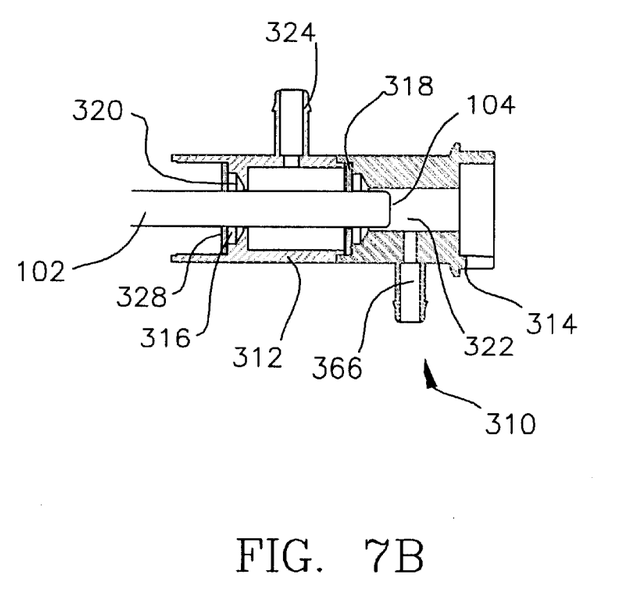

FIG. 6 shows an alternate embodiment of a cartridge 110 of the present invention. Here, a series of recesses 176 are shown disposed within the proximal chamber 120. The antimicrobial agent is disposed within the channels of the recesses 176. The recesses 176 act to hold the antimicrobial agent within the proximal chamber 120. Various configurations of the recesses can be envisioned, and all are within the scope of the present invention. For instance, the cross-section of the recess 176 can be square or dove-tail in shape. It is also to be understood that the recesses 176 can be incorporated into the embodiments described in FIGS. 7A and 7B.

Figure 9:
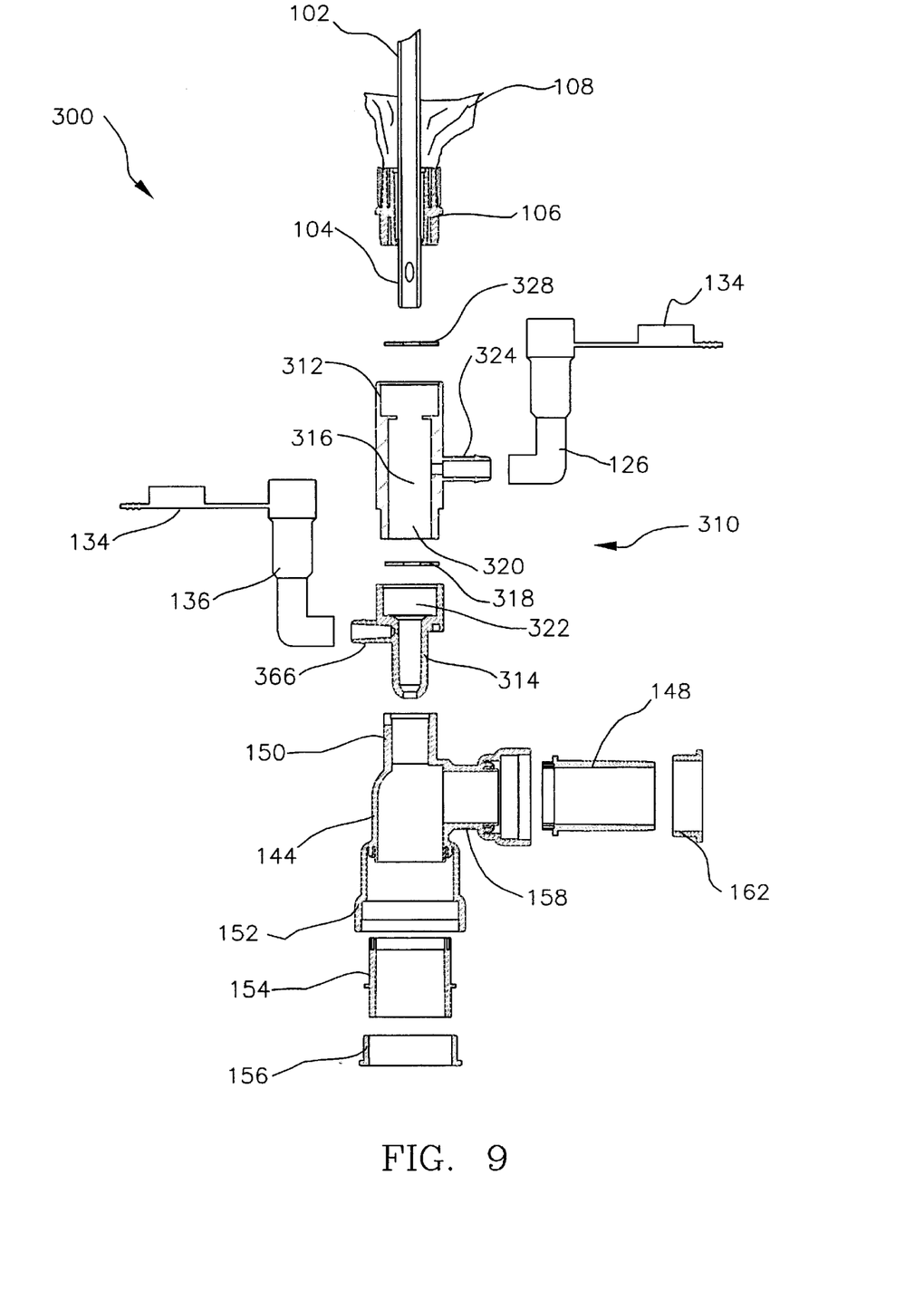
FIG. 9 is an exploded cross-sectional view of an alternate embodiment of a respiratory suction apparatus of the present invention. The drawing shows a suction catheter with a cartridge being attached to an alternate T-shaped manifold.

FIG. 9 shows an alternate embodiment of a cartridge 310 in accordance with the present invention. The embodiment in FIG. 9 resembles that disclosed in FIG. 3, only the flapper valve 142 is not incorporated. As such, the distal end 314 of the body is not configured to engage a flapper valve 142 in FIG. 9.

As shown in FIG. 9 and the previous embodiments, the cartridge designs 110 and 310 of the present invention can be configured to work with various types and styles of artificial airway manifolds and respiratory suction apparatuses. All such configurations are to be considered within the scope of the present invention.

It will be appreciated that various modifications and changes may be made to the above-described preferred embodiments of a cartridge, and a cartridge for use on a respiratory suction apparatus without departing from the scope of the following claims.

We claim:

1. A respiratory suction apparatus comprising:
    a suction catheter for removing fluids from an artificial airway of a patient by insertion and withdrawal of a distal end of the suction catheter into the artificial airway while applying negative pressure to a lumen of the suction catheter;

a cartridge accommodating passage of the suction catheter through the cartridge, the cartridge comprising:

a body having a proximal end and a distal end, the body also having a passageway leading from the proximal end to the distal end, the passageway accommodating the insertion and retraction of the suction catheter, the passageway and the proximal end defining a proximal chamber, the proximal chamber and the suction catheter moveable relative to one another, the passageway and the distal end defining a distal chamber;

an antimicrobial agent disposed in one of the distal or proximal chambers;

a port located on the body, the port communicating with one of the distal or proximal chambers in which the antimicrobial agent is disposed; and a manifold located distally of the cartridge, the manifold configured for communication with an artificial airway fitting structure attached to a patient.

2. The respiratory suction catheter apparatus as set forth in claim 1, further including a valve device located distally of the cartridge, the valve device substantially isolates the suction catheter from the manifold upon withdrawing the distal portion of the suction catheter from the manifold and applying suction through the suction catheter lumen.

3. The respiratory suction catheter apparatus as set forth in claim 2, wherein the valve device is a single flap valve.

4. The respiratory suction catheter apparatus as set forth in claim 1, wherein the body is cylindrical in shape, and the passageway in the body is substantially cylindrical in shape.

5. The respiratory suction catheter apparatus as set forth in claim 1, wherein the antimicrobial agent is a hydrogel.

6. The respiratory suction catheter apparatus as set forth in claim 1, wherein the antimicrobial agent is a quaternary amine hydrogel.

7. The respiratory suction catheter apparatus as set forth in claim 1, wherein the body has a middle seal located in the passageway between the proximal and distal ends, the body has a proximal seal located at the proximal end, and the body has a distal seal located at the distal end.

8. The respiratory suction catheter apparatus as set forth in claim 1, wherein the antimicrobial agent is disposed in the distal chamber, and the port communicates with the distal chamber.

9. The respiratory suction catheter apparatus as set forth in claim 1, wherein the antimicrobial agent is disposed in the proximal chamber, and the port communicates with the proximal chamber.

10. A respiratory suction apparatus comprising:

a suction catheter for removing fluids from an artificial airway of a patient by insertion and withdrawal of a distal end of the suction catheter into the artificial airway while applying negative pressure to a lumen of the suction catheter;

a cartridge accommodating passage of the suction catheter through the cartridge, the cartridge comprising:

a body having a proximal end and a distal end, the body also having a passageway leading from the proximal end to the distal end, the passageway accommodating the insertion and retraction of the suction catheter, the passageway and the proximal end defining a proximal chamber, the passageway and the distal end defining a distal chamber;

an antimicrobial agent disposed in one of the distal or proximal chambers;

a port located on the body, the port communicating with one of the distal or proximal chambers in which the antimicrobial agent is disposed;

a manifold located distally of the cartridge, the manifold configured for communication with an artificial airway fitting structure attached to a patient; and wherein the body has a plurality of recesses disposed therein.

11. A cartridge for use on a medical apparatus comprising:

a body having a proximal end and a distal end, the body also having a passageway leading from the proximal end to the distal end, the passageway accommodating the insertion and retraction of a surgical instrument, the passageway and the proximal end defining a proximal chamber, the passageway and the distal end defining a distal chamber;

an antimicrobial agent disposed in one of the distal or proximal chambers, the antimicrobial agent comprising at least one pharmacologically active ingredient; and a port located on the body, the port communicating with one of the distal or proximal chambers in which the antimicrobial agent is disposed.

12. The cartridge as set forth in claim 11, wherein the distal end and the proximal end of the body are adapted to be connected to a respiratory suction apparatus.

13. The cartridge as set forth in claim 11, wherein the body is substantially cylindrical in shape, and the passageway in the body is substantially cylindrical in shape.

14. The cartridge as set forth in claim 11, wherein the antimicrobial agent is a hydrogel.

15. The cartridge as set forth in claim 11, wherein the antimicrobial agent is a quaternary amine hydrogel.

16. The cartridge as set forth in claim 11, wherein the body has a middle seal located in the passageway between the proximal and distal end, the body has a proximal seal located at the proximal end, and the body has a distal seal located at the distal end.

17. The cartridge as set forth in claim 11, wherein the antimicrobial agent is disposed in the distal chamber, and the port communicates with the distal chamber.

18. The cartridge as set forth in claim 11, wherein the antimicrobial agent is disposed in the proximal chamber, and the port communicates with the proximal chamber.

19. A cartridge for use on a medical apparatus comprising:

a body having a proximal end and a distal end, the body also having a passageway leading from the proximal end to the distal end, the passageway accommodating the insertion and retraction of a surgical instrument, the passageway and the proximal end defining a proximal chamber, the passageway and the distal end defining a distal chamber;

an antimicrobial agent disposed in one of the distal or proximal chambers;

a port located on the body, the port communicating with one of the distal or proximal chambers in which the antimicrobial agent is disposed; and wherein the body has a plurality of recesses disposed therein.

20. A respiratory suction apparatus comprising:

a suction catheter for removing fluids from an artificial airway of a patient by insertion and withdrawal of a distal end of the suction catheter into the artificial airway while applying negative pressure to a lumen of the suction catheter;

a cartridge accommodating passage of the suction catheter through the cartridge, the cartridge comprising:

a body having a proximal end and distal end, the body also having a passageway leading from the proximal end to the distal end, the passageway accommodating the insertion and retraction of the suction catheter, the passageway and the proximal end defining a proximal chamber, the passageway and the distal end defining a distal chamber;

a proximal port located on the body, the proximal port communicating with the proximal chamber;

a distal port located on the body, the distal port communicating with the distal chamber;

an antimicrobial agent disposed in one of the proximal or distal chambers; and a manifold located distally of the cartridge, the manifold configured for communication with an artificial airway fitting structure attached to a patient.

21. The respiratory suction catheter apparatus as set forth in claim 20, further including a valve device located distally of the distal port, the valve device substantially isolates the suction catheter from the manifold upon withdrawing the distal portion of the suction catheter from the manifold and applying suction through the suction catheter lumen.

22. The respiratory suction catheter apparatus as set forth in claim 20, wherein the valve device is a single flap valve.

23. The respiratory suction catheter apparatus as set forth in claim 20, wherein the body is substantially cylindrical in shape, and the passageway in the body is substantially cylindrical in shape.

24. The respiratory suction catheter apparatus as set forth in claim 20, wherein the antimicrobial agent is a hydrogel.

25. The respiratory suction catheter apparatus as set forth in claim 20, wherein the antimicrobial agent is a quaternary amine hydrogel.

26. The respiratory suction catheter apparatus as set forth in claim 20, wherein the body has a middle seal located in the passageway between the proximal and distal ends, and the body has a proximal seal located in the passageway at the proximal end.

27. The respiratory suction catheter apparatus as set forth in claim 20, wherein the body has a plurality of recesses disposed therein.

28. The respiratory suction catheter apparatus as set forth in claim 20, wherein the antimicrobial agent is disposed in the distal chamber.

29. The respiratory suction catheter apparatus as set forth in claim 20, wherein the antimicrobial agent is disposed in the proximal chamber.

30. A cartridge for use on a medical apparatus comprising:

a body having a proximal end and a distal end, the body also having a passageway leading from the proximal to the distal end, the passageway accommodating the insertion and retraction of a surgical instrument, the passageway and the proximal end defining a proximal chamber, the passageway and the distal end defining a distal chamber;

a proximal port located on the body, the proximal port communicating with the proximal chamber;

a distal port located on the body, the distal port communicating with the distal chamber; and an antimicrobial agent disposed in one of the proximal or distal chambers, the antimicrobial agent comprising at least one pharmacologically active ingredient.

31. The cartridge as set forth in claim 30, wherein the distal end and proximal end of the body are adapted to be connected to a respiratory suction apparatus.

32. The cartridge as set forth in claim 30, wherein the body is substantially cylindrical in shape, and the passageway in the body is substantially cylindrical in shape.

33. The cartridge as set forth in claim 30, wherein the antimicrobial agent is a hydrogel.

34. The cartridge as set forth in claim 30, wherein the antimicrobial agent is a quaternary amine hydrogel.

35. The cartridge as set forth in claim 30, wherein the body has a middle seal located in the passageway between the proximal and distal ends, and the body has a proximal seal located in the passageway at the proximal end.

36. The cartridge as set forth in claim 30, wherein the antimicrobial agent is disposed in the distal chamber.

37. The cartridge as set forth in claim 30, wherein the antimicrobial agent is disposed in the proximal chamber.

38. A cartridge for use on a medical apparatus comprising:

a body having a proximal end and a distal end, the body also having a passageway leading from the proximal to the distal end, the passageway accommodating the insertion and retraction of a surgical instrument, the passageway and the proximal end defining a proximal chamber, the passageway and the distal end defining a distal chamber;

a proximal port located on the body, the proximal port communicating with the proximal chamber;

a distal port located on the body, the distal port communicating with the distal chamber;

an antimicrobial agent disposed in one of the proximal or distal chambers; and wherein the body has a plurality of recesses disposed therein.

* * * * *

UNITED STATES PATENT AND TRADEMARK OFFICE
CERTIFICATE OF CORRECTION

PATENT NO. : 6,588,425 B2
DATED : July 8, 2003
INVENTOR(S) : Cameron G. Rouns et al.

It is certified that error appears in the above-identified patent and that said Letters Patent is hereby corrected as shown below:

<u>Title page,</u>
Item [75], Inventors, please add -- Jeffrey Alan Bennett and James J. Perrault --.

Signed and Sealed this

Eleventh Day of May, 2004

JON W. DUDAS
*Acting Director of the United States Patent and Trademark Office*